United States Patent [19]
Krupa

[11] Patent Number: 5,599,308
[45] Date of Patent: Feb. 4, 1997

[54] INTERMITTENT VACUUM REGULATOR WITH TIMING MODULE

[76] Inventor: Michael A. Krupa, 4070 Heather Ct., Northampton, Pa. 18067

[21] Appl. No.: 530,933

[22] Filed: Sep. 19, 1995

[51] Int. Cl.⁶ .................................................. F16K 17/00
[52] U.S. Cl. ............................................ 604/118; 604/120
[58] Field of Search ................................. 604/118, 119, 604/120, 317, 319, 320; 137/624.11, 624.13, 103, 907

[56] References Cited

U.S. PATENT DOCUMENTS 4,930,997  6/1990  Bennett .
4,988,336  1/1991  Kohn .

OTHER PUBLICATIONS

The Principles of Vacuum & Its Use in the Hospital Environment Ohmeda 12 page brochure 1985.
Pediatric Vacutron — Continuous/Intermittent Allied Healthcare Products, Inc. Aug. 1988.
Operation Manual For Intermittent Suction Unit Published By Ohio Medical Products, Date Unknown.

*Primary Examiner*—Sam Rimell
*Attorney, Agent, or Firm*—Caesar, Rivise, Bernstein, Cohen & Pokotilow, Ltd.

[57] ABSTRACT

A vacuum regulator having a timing module that provides intermittent vacuum and is modular in design permitting easy removal and replacement without having to disassemble the entire vacuum regulator.

6 Claims, 7 Drawing Sheets

ON STATE

FIG. 10

OFF STATE

FIG. 11

ON STATE

FIG. 12

OFF STATE

INTERMITTENT VACUUM REGULATOR WITH TIMING MODULE

FIELD OF THE INVENTION

This invention relates generally to the field of medical pressure devices, more particularly, to an intermittent vacuum regulator that intermittently turns on the vacuum delivered through a catheter and intermittently turns off the vacuum on a regular timing cycle to permit the release of blockages.

BACKGROUND OF THE INVENTION

The aspiration of fluids from a patient is accomplished by providing a vacuum source through a catheter to the internal body area of the patient requiring aspiration. Typically, unregulated hospital vacuum line pressure is approximately between 19" to 25" of mercury (Hg.).

The use of vacuum regulators as medical devices is well known to achieve such aspiration of fluids. Generally such vacuum regulators are attached to a vacuum outlet in the wall of the patient's hospital room. Known vacuum suction regulators include a variable vacuum regulator, the vacuum gauge and a mechanical mechanism which cycles the vacuum on and off at predetermined timed intervals. Certain of these vacuum regulators are mechanical devices which use the vacuum source as a means of powering the cycling mechanism. Through practice it has been determined that a preferred off and on cycle is at such ratio that the vacuum regulator will be effective for twice the time that it is on as compared with the time that it is off. This two to one ratio is the ratio usually employed in currently available vacuum regulators even where this ratio can be varied as in an available intermittent vacuum regulators such as the one marketed under the name Vacutron sold by Allied Healthcare Products, Inc. of St. Louis, Mo.

Such known mechanical intermittent vacuum regulators achieve vacuum cycling by means of precise air flow into and out of an air chamber. In the Vacutron intermittent regulator there is a spring loaded mechanism in combination with a diaphragm assembly that controls the rotating valve. This mechanism is rather large and is not modular, i.e., failure of any of the springs, clevis arms, diaphragm, etc. requires the disassembly of the entire mechanism. A field service representative would either have to be called out or the faulty unit returned to the manufacturer for repair. Such a device allows the volume in the chamber to increase and decrease on a periodic basis. The diaphragm will be connected to a mechanism that cycles to the vacuum on and off. In order to control the on/off time periods two needle valves control the air flow into and out of the diaphragm. Problems arise with such known devices due to the fact that the on/off time periods are fairly long and the total air chamber volume is quite small. Therefore, in order to operate at such small flow rates, the valve openings themselves are also small. The small valve openings make the timing of the intermittent regulator sensitive to clogging by means of small dirt particles in the vacuum line.

There are other types of known mechanical intermediate vacuum regulators which utilize vacuum as a means to power the regulators. However, they are operated by a pneumatic logic type system. Such devices are also subject to becoming clogged by means of small dirt particles.

OBJECTS OF THE INVENTION

Accordingly, it is the general object of this invention to provide an apparatus and a method of use which addresses the aforementioned needs.

It is a further object of this invention to provide a timing module that can operate from a varying vacuum line pressure of 19"–25" Hg.

Another object of the present invention is to provide an apparatus that avoids the complexity of prior devices and yet retains the essential functions of the prior devices as well as being easily serviced.

SUMMARY OF THE INVENTION

These and other objects of the present invention are achieved by providing an intermittent vacuum regulator with a timing module wherein the timing module is easily separated from the main body of the intermediate vacuum regulator. Such main body includes a main body housing which holds a vacuum gauge or vacuum indicating means as well as the mode switching and vacuum adjustment means. The timing module includes a needle valve to permit variation of the various 2:1 ratios.

The timing module is detachably secured to the main body housing and in the preferred embodiment includes a ceramic switching valve comprised of ceramic discs. There are two modes of operation, namely, an "off" mode (no vacuum to patient) and an "on" mode (which allows vacuum to patient).

During the "off" mode the vacuum is ported to a diaphragm assembly via the ceramic switching valve. In this mode the vacuum also evacuates the diaphragm chamber at a rate determined by a needle valve opening in the base of the diaphragm chamber. This has the effect of pulling down on the diaphragm to compress a spring. A push rod is provided and is connected to the diaphragm. In the "off" mode where the vacuum has evacuated the diaphragm chamber, the push rod moves downwardly and rotates a lever arm counterclockwise through a gear interconnect. There is a toggle spring which is connected to the lever arm. Once the two pivot points of the toggle spring at the lever arm and ceramic valve cross over the center line of each other, the ceramic valve will flip to the "on" mode.

During the "on" mode (vacuum to patient) the ceramic valve is positioned to port vacuum to the patient. The diaphragm chamber is then vented to atmosphere via the ceramic switching valve. The compressed diaphragm spring then pushes on the diaphragm which has the effect of pulling atmospheric air into the chamber at a rate determined by the needle valve opening. This allows the diaphragm to move upwardly. The push rod (attached to the diaphragm) also moves upwardly to rotate the lever arm clockwise by the gear interconnect. Once the two pivot points of the lever arm toggle spring and the ceramic valve cross over the center line of each other, the valve flips to the "off" mode.

An important feature of the invention is that the components of the timing module are mounted on a back plate which is secured to the main regulator housing by screws. Hospital personnel can easily remove these screws and replace the timing module in the event there is a problem in the operation of the intermittent regulator, such as clogged passageways. This is a significant improvement over prior art devices which would require sophisticated servicing.

DESCRIPTION OF THE DRAWINGS

Other objects and many of the attendant advantages of this invention will be readily appreciated as the same becomes better understood by reference to the following detailed description when considered in connection with the accompanying drawings wherein.

DESCRIPTION OF THE PREFERRED EMBODIMENT OF THE INVENTION

Referring now in greater detail to the various figures of the drawing wherein like reference characters refer to like parts, an intermittent vacuum regulator (hereinafter "IVR") with timing module constructed in accordance with the present invention is shown generally at 20 in FIG. 1.

The face plate 22 of the IVR 20 comprises a vacuum gauge 24 and a control knob 26. As shown in FIG. 2, the control knob 26 comprises a mode select switch 28 and a regulator adjusting knob 30. The mode select switch 28 has three settings (OFF, REGULATE, INTERMITTENT) that totally shuts off the vacuum (OFF), or permits the user to select a particular vacuum level (REGULATE) or intermittently turns the vacuum on and off at a 2:1 ratio (INTERMITTENT). Setting the mode select switch 28 to the REGULATE mode delivers a regulated vacuum (to a level set by the regulator adjusting knob 30 as indicated on the gauge 24) on a continuous basis to the patient. Setting the mode select switch 28 to the INTERMITTENT mode delivers a regulated vacuum on an intermittent basis to the patient.

Figures 1, 2:
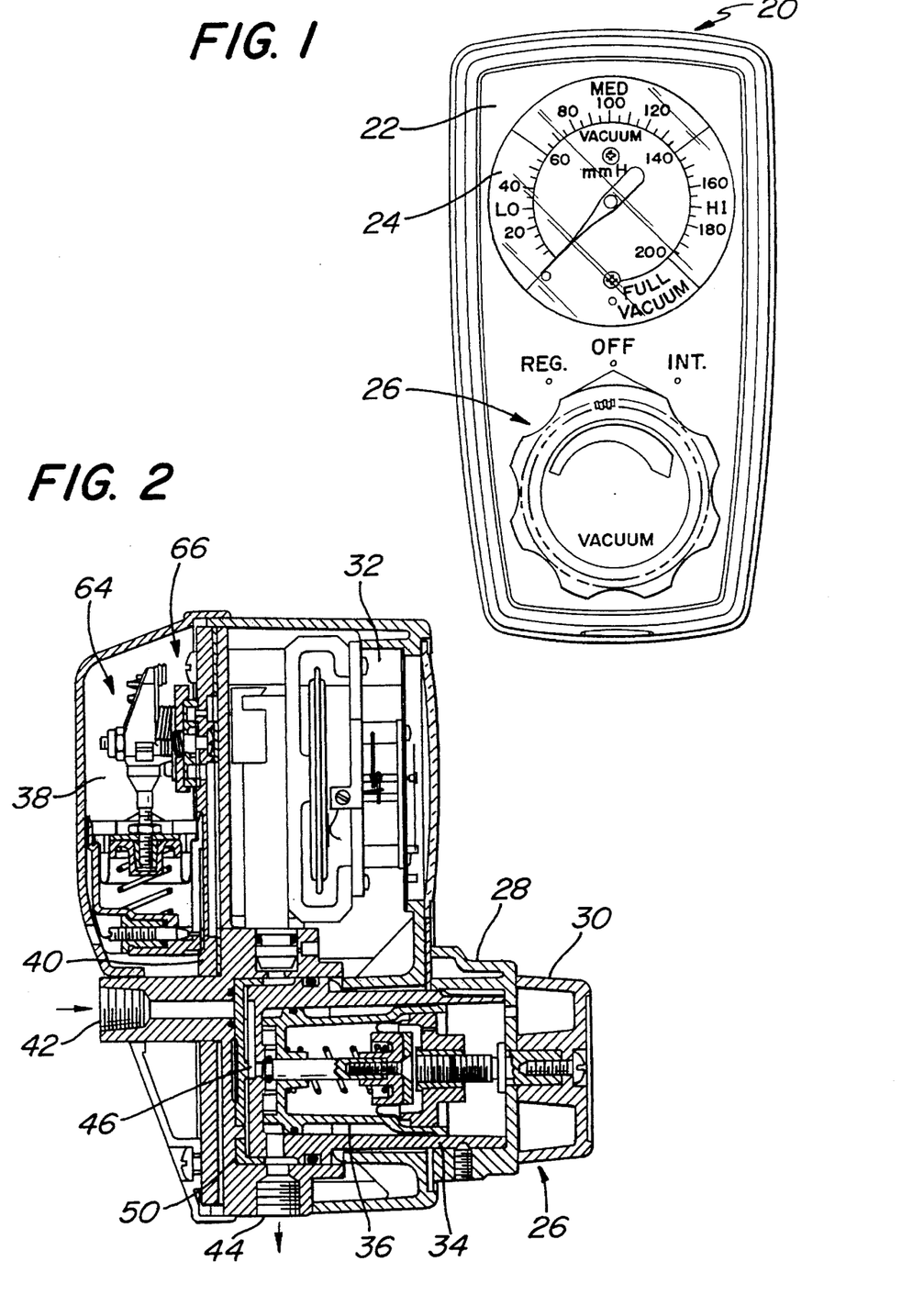
FIG. 1 is a front view showing the front face of the vacuum regulator of the present invention.
FIG. 2 is a cross-sectional side view of the present invention.
Figures 3, 4:
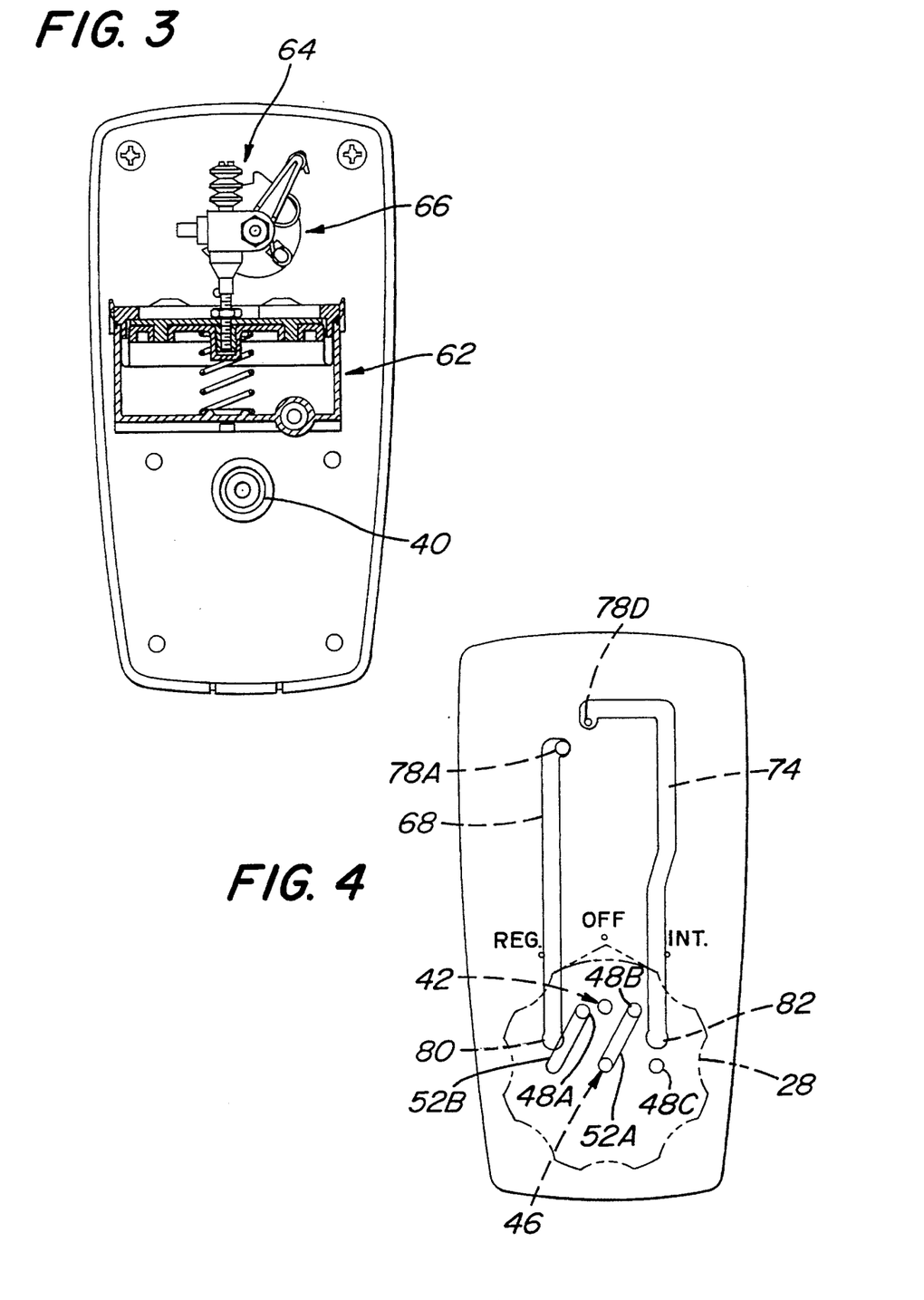
FIG. 3 is a plan view of the timing module portion of the present invention.
FIG. 4 is a phantom view of the pneumatic coupling portion of the timing module when the mode select switch in the OFF mode.
Figures 5, 6:
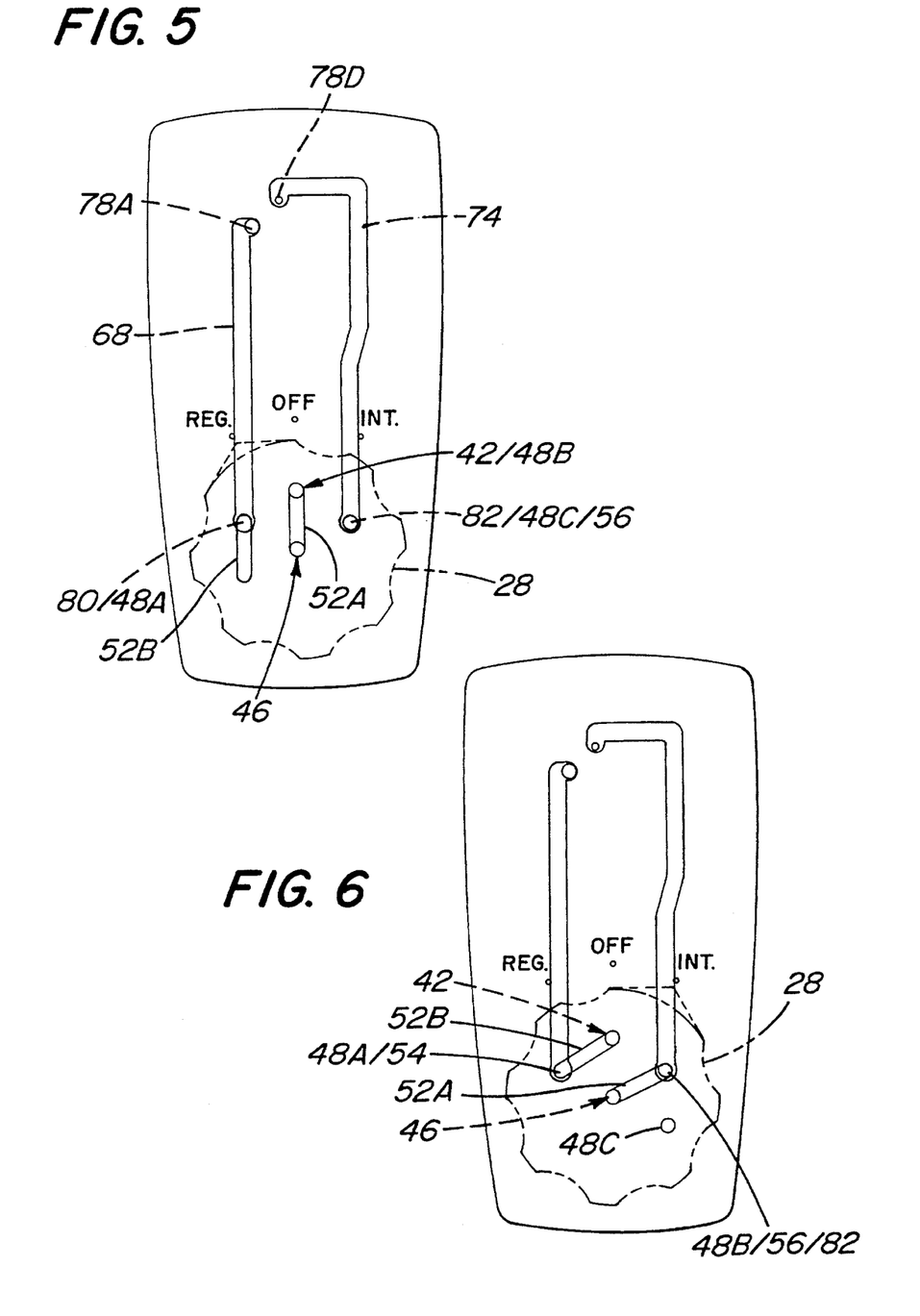
FIG. 5 is a phantom view similar to FIG. 4 when the mode select switch in the REGULATE mode.
FIG. 6 is a phantom view similar to FIG. 4 when the mode select switch in the INTERMITTENT mode.

As shown more clearly in FIG. 2, the IVR 20 basically comprises a gauge module 32, a switching module 34 that houses a regulating module 36 controlled by the control knob 26, and a timing module 38 that couple to a main casting 40. An input vacuum line (not shown) delivers hospital vacuum (19" to 25" Hg.) to the IVR 20 via an inlet coupling 42. Regulated vacuum, whether continuous or intermittent, is then delivered to the patient from an outlet coupling 44 via an output line (not shown). As shown in FIGS. 4–6, selection by the user, via the mode select switch 28, of one of the three modes (OFF, REGULATE, INTERMITTENT) causes the inlet coupling 42 to be coupled to no port (FIG. 4, OFF mode), to a regulator input port 46 (FIG. 5, REGULATE mode), or to the timing module 38 (FIG. 6, INTERMITTENT mode) which then feeds the hospital vacuum to the regulator input port 46.

In particular, the port holes 48A, 48B and 48C are located in a seal cap 50 (FIG. 2), driven by the mode select switch 28, that aligns the inlet coupling 42 accordingly. In the OFF mode (FIG. 4), the inlet coupling 42 is not coupled to the regulator input port 46 and as such no vacuum is being delivered to the patient. In the REGULATE mode (FIG. 5), the inlet coupling 42 is directly coupled to the regulator input port 46 by a coupling 52A, with the port hole 48B being aligned with the inlet coupling 42, thereby delivering hospital vacuum to the regulating module 36. In the INTERMITTENT mode (FIG. 6), the inlet coupling 42 is coupled to a vacuum input port 54 of the timing module 38 by a coupling 52B and the vacuum outlet port 56 of the timing module 38 is coupled to the regulator input port 46 by the coupling 52A, thereby delivering an intermittent hospital vacuum to the regulating module 36.

It should be understood that when the INTERMITTENT mode is selected, the timing module 38 (as will be discussed in detail later) converts the continuous hospital vacuum into an intermittent vacuum having an ON time (i.e., vacuum is "on") that is twice the OFF time (i.e., vacuum is "off"). Once this intermittent vacuum is created by the timing module 38, the intermittent vacuum is then fed to the regulating module 36 via the regulator input port 46, where the ON portion of the intermittent vacuum is regulated to a level that is set by the regulator adjusting knob 30. Therefore, any subsequent reference that states that the intermittent vacuum is delivered to the patient implies that the intermittent vacuum is actually communicated to the regulating module 36 where the ON portion of the intermittent vacuum is regulated to the level set by the regulator adjusting knob 30 and then delivered to the patient.

It should also be noted at this point that the generation of a continuous regulated vacuum is well-known in the art and as such will not be discussed hereinafter. However, the generation of an intermittent vacuum, described in the manner set forth below, that is then regulated is the novel aspect of the IVR 20.

Figures 7, 8:
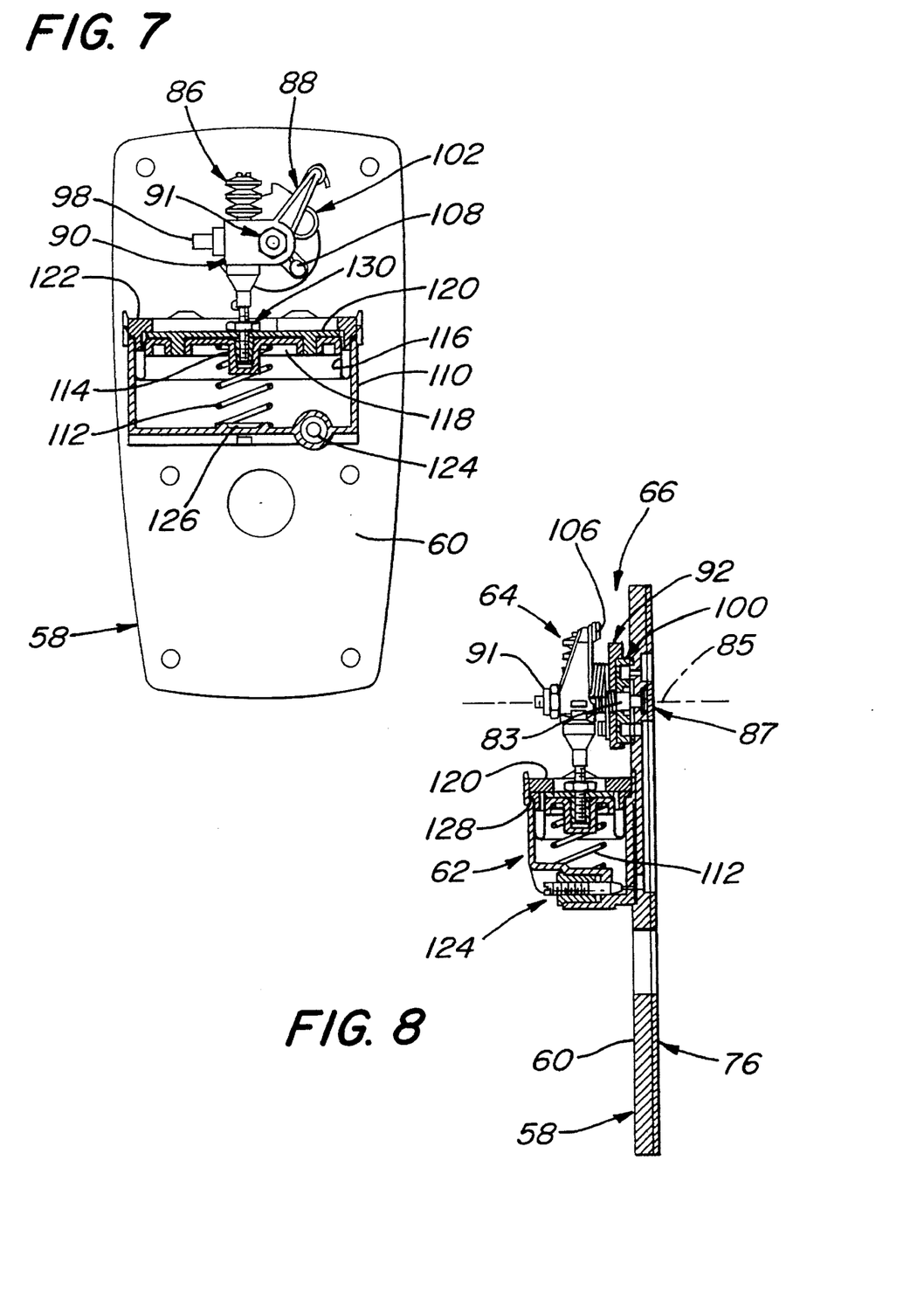
FIG. 7 is an enlarged plan view of the timing module.
FIG. 8 is a cross-sectional side view of the timing module.
Figures 11, 12:
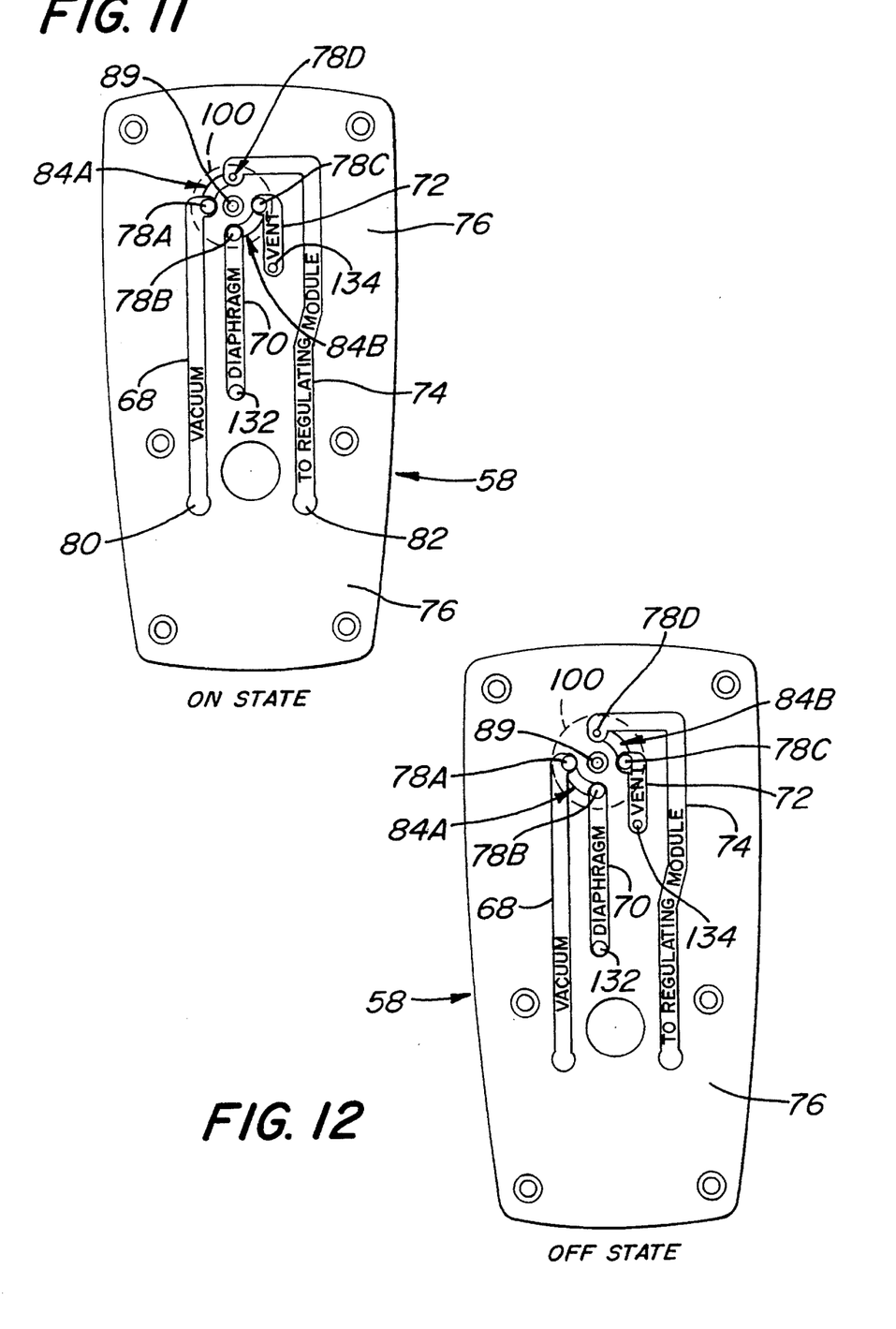
FIG. 11 is a plan view of the back plate of the timing module depicting ambient pressure flow to the diaphragm assembly of FIG. 9.
FIG. 12 is a plan view of the back plate of the timing module depicting vacuum flow to the diaphragm assembly of FIG. 10.

The timing module 38 is operative only when the user selects the INTERMITTENT setting of the mode select switch 28. As can be seen in FIGS. 7–8, the timing module 38 comprises a base plate 58 having a front side 60 that supports a diaphragm assembly 62, valve control means 64 and valve means 66. The back side (FIGS. 11 and 12) of the base plate 58 contains a vacuum channel 68, a diaphragm channel 70, a vent channel 72 and a regulator channel 74. It should be understood that a gasket 76, having the same shape as the back side of the base plate 58 and with channels corresponding to channels 68–74, is fixedly secured to the back side of the base plate 58. When the timing module 38 is installed in the IVR 20, the gasket 76 is in contact with the main casting 40 to form a tight seal.

In addition, there are four port holes of a valve disk 78 that are in pneumatic communication with the valve means 66. The valve disk 78 is fixedly secured within the base plate 58. Port hole 78A is an outlet for the vacuum channel 68, port hole 78B is an inlet hole to the diaphragm assembly 62, port hole 78C is outlet hole for ambient pressure and port hole 78D is an inlet hole to the patient channel 74; port hole 78D comprises an 8 liters/minute restrictor. It should be noted that when the timing module 38 is coupled to the IVR 20, the vacuum input port 54 (FIGS. 4–6) is disposed directly over the lower end 80 of the vacuum channel 68, thereby bringing hospital vacuum into the timing module 38 via the vacuum channel 68; moreover, the vacuum output port 56 (FIGS. 4–6) is disposed directly over the lower end 82 of the regulator channel 74, thereby providing the intermittent vacuum to the regulator input port 46.

Figure 14:
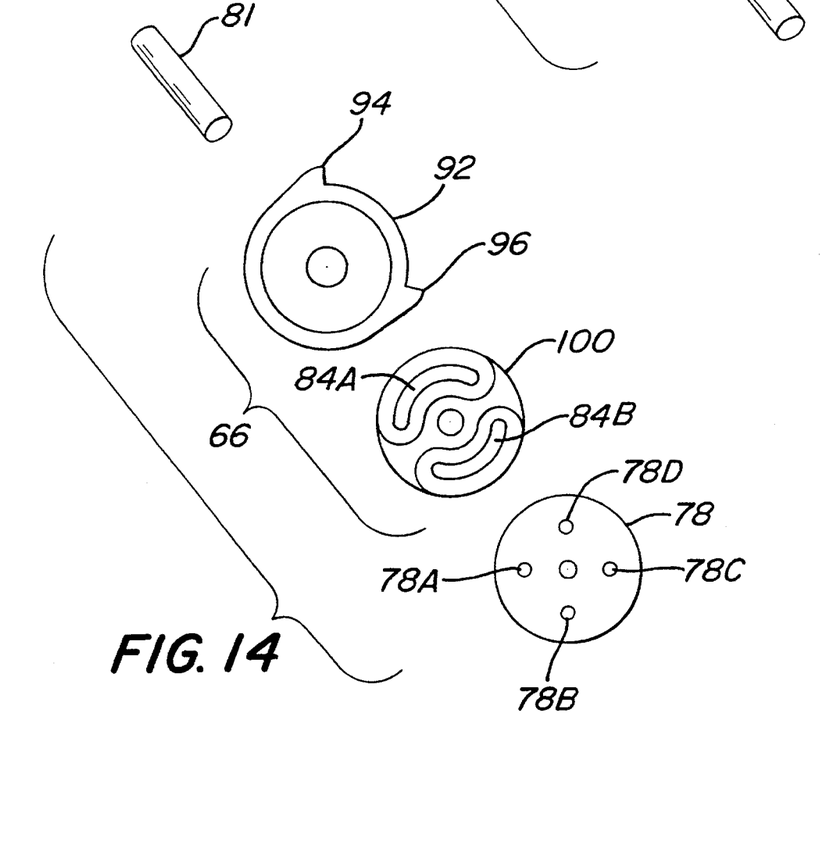

The intermittent "ON/OFF" cycle is established when the valve means 66 couples the four port holes (78A–78D) of the valve disk 78 in particular pairs. In particular, during the "ON" portion of the intermittent cycle (FIG. 9), the valve means 66 comprises a rotatable valve coupler 100 having a first coupling 84A (FIG. 11) that operates to couple port hole 78A to port hole 78D and has a second coupling 84B that operates to couple port hole 78B to port hole 78C; this coupling action delivers vacuum to the patient while porting the diaphragm assembly 62 to ambient pressure. As shown in FIG. 14, the valve disk 78 has a face in contact with the couplings 84A and 84B of the valve coupler 100. During the "OFF" portion of the intermittent cycle (FIG. 10), the first coupling 84A (FIG. 12) operates to couple port hole 78A to port hole 78B while the second coupling 84B operates to couple port hole 78C to port hole 78D; this coupling action ports vacuum to the diaphragm assembly 62 while delivering ambient pressure to the patient (i.e., shutting off the vacuum to the patient). Thus, as will be discussed in detail later, the valve means 66 is always in either one of two states: an ON state, where port holes 78A and 78D are coupled together and port holes and 78B and 78C are coupled together; an OFF state, where port holes 78A and 78B are coupled together and port holes 78C and 78D are coupled together. The valve control means 64, in combination with the diaphragm assembly 62, act to cycle the valve means 66 between the ON/OFF states at a rate that is always in the ratio of 2:1 (i.e., the vacuum is delivered to the patient for twice the time that it is off). As will also be discussed later, the actual ON/OFF times can be varied by the user (e.g., 5 seconds ON/2.5 seconds OFF, 8 seconds ON/4 seconds OFF, 16 seconds ON/8 seconds OFF) but these ON/OFF times are always in the ratio of 2:1.

Figure 13:
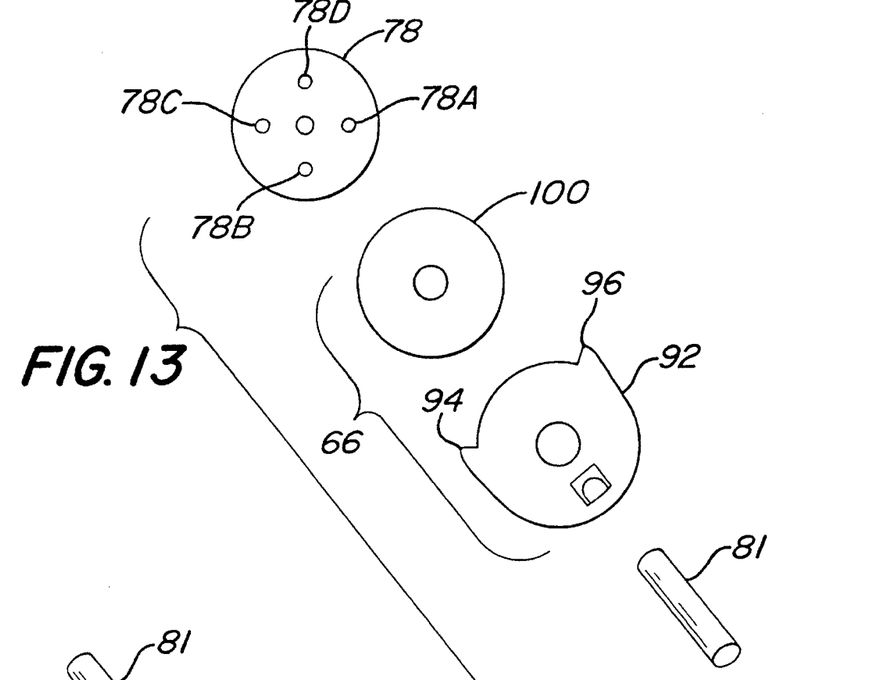
FIGS. 13 and 14 are views respectively showing the valve disk 78, rotatable valve coupler 100 and the circular valve housing 92 in operative spaced relation to each other and taken from a first side and a second side.

The valve control means 64 (FIGS. 7 and 8) comprises a push rod 86 and a geared lever arm 88 (e.g., a pinion gear having a portion of its circumference integral with a lever arm) coupled to a lever arm) that are coupled in a worm gear fashion. Downward vertical displacement of the push rod 86 causes the geared lever arm 88 to rotate in a counterclockwise direction about an axis 85 while upward vertical displacement of the push rod 86 causes the geared lever arm 88 to rotate in a clockwise direction. The rotation of the geared lever arm 88 is transferred to the valve means 66 by a bushing 81 that is directly coupled between the geared lever arm 88 and the circular valve housing 92, to be discussed below. Vertical displacement of the push rod 86 is controlled by the diaphragm assembly 62 as will be discussed later. A rod bracket 90 ensures that the push rod 86 displacement is entirely vertical with no tilting. (It should be noted that the bushing 81 (FIGS. 13–14) is hidden from view in FIG. 8 since it is located inside a load spring 83.)

Figure 9:
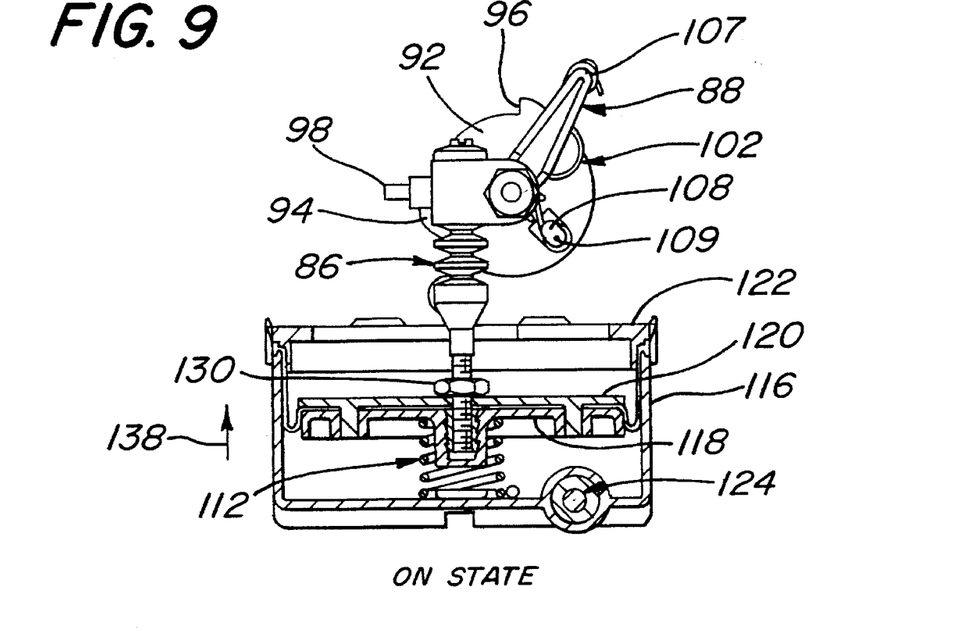
FIG. 9 is a cross-sectional view of the diaphragm assembly when ambient pressure is ported therein.
Figure 10:
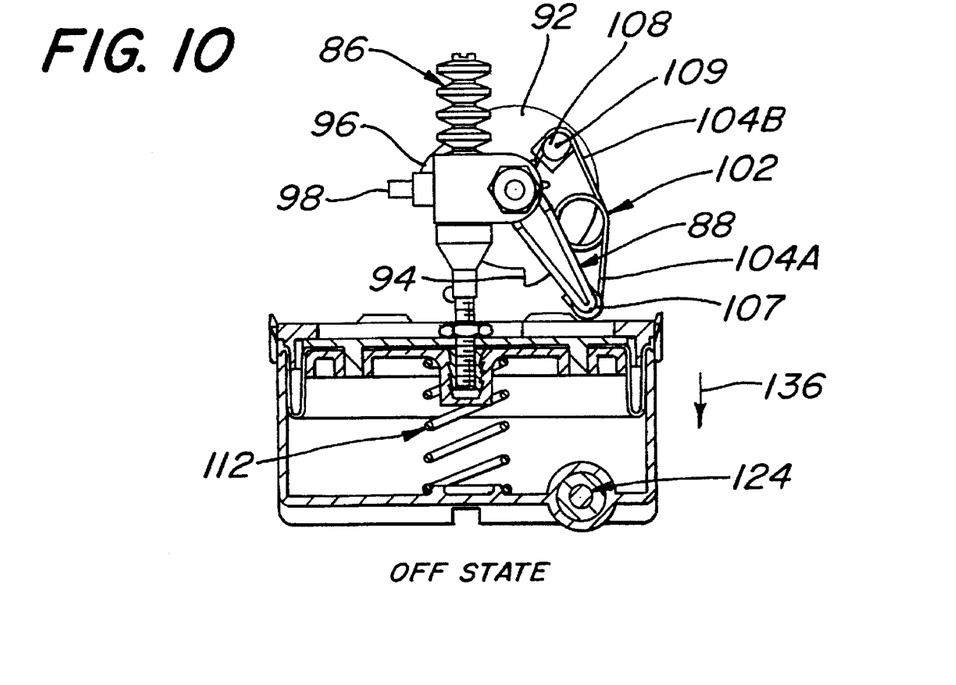
FIG. 10 is a cross-sectional view of the diaphragm assembly when vacuum is ported therein.

The valve means 66 (FIGS. 13–14) comprises a ceramic circular housing 92 (FIGS. 9, 10, 13 and 14) having a first stop 94 and a second stop 96 located at predetermined positions on the periphery of the housing 92. These stops 94 and 96 alternately engage a base plate stop 98 that is secured to the front side 60 (FIG. 7) of the base plate 58. Permanently secured within the housing 92 is the circular valve coupler 100 (FIGS. 13–14) that includes the first coupling 84A (FIG. 14) and the second coupling 84B (FIG. 14). Hence, the housing 92/valve coupler 100 rotate together as a unit as determined by the rotation of geared lever arm 88 about the axis 85. The predetermined positions of the stops 94 and 96 along the periphery of the housing 92 are designed to position the first coupling 84A and the second coupling 84B over the corresponding port holes 78A–78D, as discussed previously. Thus, during the ON portion of the intermittent cycle, the stop 94 is in contact with the base plate stop 98 (FIG. 9). During the OFF portion of the intermittent cycle, the stop 96 is in contact with the base plate stop 98 (FIG. 10). As stated above a bushing 81 (FIGS. 13–14) directly couples the geared lever arm 88 to the valve means 66. Therefore, as the geared lever arm 88 rotates about the axis 85, the bushing 81 allows the valve means 66 to rotate about the same axis 85. Both the valve control means 64 and the valve means 66 are rotatably secured along the axis 85 by, among other things, a screw 87 that is inserted in an opening 89 (FIGS. 11–12) through the valve means 66, through the bushing 81, through the geared lever arm 88 and then secured by a nut 91.

The counterclockwise/clockwise motion of the lever arm 88 is what controls the valve means 66. In particular, a toggle spring 102 comprises spring arms 104A and 104B (FIG. 10). The spring arm 104A is coupled to the lever arm tip 106 (FIG. 8), forming a pivot point 107, (FIGS. 9–10), and the spring arm 104B is coupled to the ceramic circular housing 92 via a catch 108, forming a pivot point 109. The toggle spring 102, in combination with the stops 94/96 contacting the base plate stop 98, cause the valve means 66 to "snap" or "flip" into the ON state or into the OFF state. Hence, there is no in-between state of the valve means 66. As the lever arm 88 rotates either in a clockwise motion or in a counterclockwise motion, once the spring arm 104A (attached to the pivot point 107) and the spring arm 104B (attached to the pivot point 109) cross over the center line of each other, the valve means 66 flips to the OFF state or to the ON state, respectively.

The diaphragm assembly 62 controls the vertical displacement of the push rod 86. As shown in FIG. 7, the diaphragm assembly 62 comprises a housing 110, a spring 112, an insert 114, a rolling diaphragm 116, an inner plate 118, an outer plate 120, a cover 122 and a needle valve 124. One end of the push rod 86 is secured within the threaded insert 114 which in turn is seated within the inner plate 118. The inner plate 118 is disposed on top of the spring 112. The other end of the spring 112 is secured around a boss 126 on the bottom of the housing 110. The rolling diaphragm 116 is disposed over top of the inner plate 118; the edges of the rolling diaphragm 116 are secured in a shoulder 128 that encompasses the inside periphery of the housing 110. The rolling diaphragm 116 is sandwiched between the inner plate 118 and the outer plate 120. The push rod 86 is secured to the outer plate 120 with a nut 130. The cover 122 forms an air tight seal around the edges of the rolling diaphragm 116 against the shoulder 128. Thus, the timing rod 86, the insert 114, the inner plate 118, the rolling diaphragm 116 and the outer plate 120 form a vertically-displaceable assembly that is driven by the pressure present within the housing 110 against an upward biasing force of the spring 112.

The needle valve 124 (FIG. 8) controls the rate at which the vacuum evacuates the diaphragm assembly. In particular, a diaphragm assembly input port hole 132 (FIGS. 11 and 12) at one end of the diaphragm channel 70 is coupled to the needle valve 124 (FIG. 8) through the base plate 58. Hence, when the valve means 66 is positioned in the OFF state, the vacuum is ported to the diaphragm assembly 62 and the position of the needle valve 124 controls the rate of evacuation by the vacuum. On the other hand, when the valve means 66 is in the ON state, the diaphragm channel 70 is coupled to the vent channel 72 which has an ambient pressure port hole 134 that brings ambient pressure into the diaphragm assembly 62 also through the needle valve 124; this permits the vertically-displaceable assembly to move upward in the direction of the bias from the spring 112. A porous filter (not shown) is included at the input port hole 132 to filter out, and thereby prevent, any blockage of the needle valve 124; this porous filter does not affect the operation of the vacuum/vent flows.

In a preferred embodiment of the timing module 38, the dimensions/characteristics of the following components of the timing module 38 determine the 2:1 timing ratio:

length of the geared lever arm 88, from the center line of the gear (of geared lever arm 88) to the center line of the pivot point 107: 0.710";

a 0.384" diameter gear (of geared lever arm 88) with 30° gear spacing interfaced with a 0.300" diameter push rod 86;

distance from the center line of the circular valve housing 92 to the center line of the pivot attachment point 109: 0.339";

strength of the toggle spring 102 (from the center line of the pivot point 107 to the center line of the pivot point 109): 0.900" made from 0.024" diameter stainless steel wire having a diameter of 0.250" consisting of 5 coils;

an average approximate volume of the diaphragm assembly housing 110: 1.2 inches$^3$;

the spring 112 (inside the diaphragm assembly housing 110) having a free length of 1.325" with an outside diameter of 0.500" comprising a stainless steel wire of a 0.035" diameter consisting of 5½ coils;

rolling diaphragm 116 being of a material thickness of 0.018" in a nominal rectangular configuration of 1.830"×0.720".

Operation of the timing module 38 is as follows: During the OFF state, (i.e., FIG. 10, no vacuum to the patient), the vacuum is ported to the diaphragm assembly 62 via the valve means 66, thereby causing the vertically-displaceable assembly to move downward in the direction indicated by the arrow 136. The vacuum evacuates the diaphragm assembly 62 at a rate determined by the needle valve 124 opening and pulls down on the rolling diaphragm 116, thereby compressing the spring 112. The push rod 86 which is connected to the rolling diaphragm 116 moves downward and rotates geared lever arm 88 counterclockwise. Once the two pivot points of the toggle spring 102 cross over the center line of each other, the valve means 66 flips to the ON state.

During the ON state (FIG. 9, i.e., vacuum is being delivered to the patient), the valve means 66 is positioned to port the vacuum to the regulating module 36. The diaphragm assembly 62 is then vented to ambient pressure, thereby causing the vertically-displaceable assembly to move in the direction indicated by the arrow 138. The compressed spring 112 within the diaphragm assembly 62 then pushes on the rolling diaphragm 116 and pulls ambient pressure air into the diaphragm assembly 62 at a rate determined by the needle valve 124 opening, thereby allowing the rolling diaphragm 116 to move upward. The push rod 86 is therefore driven upward and rotates the geared lever arm 88 clockwise. Once the two pivot points of the toggle spring 102 cross over the center line of each other, the valve means 66 flips to the OFF state.

It should be noted that the user can vary the length of time of the ON and OFF state by adjusting the needle valve 124 (e.g., 5 seconds ON/2.5 seconds OFF, 8 seconds ON/4 seconds OFF, 16 seconds ON/8 seconds OFF). However, the valve control means 64 (i.e., the push rod 86, geared lever arm 88, toggle spring 102, etc.) and the diaphragm assembly 62 (i.e., the toggle spring 102, the spring 112, the rolling diaphragm 116, etc.) are designed to fix the ON/OFF states at a 2:1 ratio.

Without further elaboration, the foregoing will so fully illustrate my invention that others may, by applying current or future knowledge, readily adopt the same for use under various conditions of service.

I claim:

1. An intermittent vacuum regulator having a timing module in combination with a valve means for controlling the position of said valve means between one of two states, said module comprising:

a base plate having a plurality of channels and apertures for conveying vacuum pressure in a first state or ambient state in a second state;

a diaphragm assembly coupled thereto;

a gear coupled to a lever arm that is in contact with said valve means;

said diaphragm assembly having a diaphragm, coupled to said gear, that is exposed to a vacuum source and ambient pressure alternately said diaphragm disposed within said diaphragm assembly to form a movable wall of said diaphragm assembly, said alternating exposure causing said gear to move in a first direction or a second direction, respectively, movement in said first direction defining an off time and movement in said second direction defining an on time and also defining a timing ratio.

2. The timing module of claim 1 wherein said valve means comprises a stationary disk having a plurality of apertures coupled to respective channels in said base plate.

3. The timing module of claim 2 wherein said valve means further comprises a housing including a circular valve having couplings attached thereto, said housing being rotatable to pneumatically couple said plurality of apertures of said stationary disk in respective pairs.

4. The timing module of claim 1 wherein said timing ratio is defined as 2:1.

5. The timing module of claim 1 being modular to permit the removal of said timing module from the intermittent vacuum regulator and the replacement of said timing module with another timing module within the intermittent vacuum regulator.

6. The timing module of claim 1 further comprising a needle valve coupled to said diaphragm assembly, said needle valve permitting the establishment of a plurality of 2:1 ratios.

\* \* \* \* \*

UNITED STATES PATENT AND TRADEMARK OFFICE
CERTIFICATE OF CORRECTION

| | | |
|---|---|---|
| PATENT NO. | : 5,599,308 | Page 1 of 1 |
| APPLICATION NO. | : 08/530933 | |
| DATED | : February 4, 1997 | |
| INVENTOR(S) | : Michael A. Krupa | |

It is certified that error appears in the above-identified patent and that said Letters Patent is hereby corrected as shown below:

In Claim 1, at Column 8, Line 28, please replace "ambient state" with -- ambient pressure --.

Signed and Sealed this

Thirtieth Day of November, 2010

David J. Kappos
*Director of the United States Patent and Trademark Office*